(12) United States Patent
Dardzinski

(10) Patent No.: US 7,092,082 B1
(45) Date of Patent: Aug. 15, 2006

(54) METHOD AND APPARATUS FOR INSPECTING A SEMICONDUCTOR WAFER

(75) Inventor: Victor C. Dardzinski, Saugus, MA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 188 days.

(21) Appl. No.: 10/723,585

(22) Filed: Nov. 26, 2003

(51) Int. Cl.
  *G01N 21/88* (2006.01)
  *G01V 8/00* (2006.01)
(52) U.S. Cl. .............. 356/237.5; 359/642; 250/559.04; 250/201.3
(58) Field of Classification Search .. 356/237.1–237.6; 250/559.04, 559.4, 559.41, 559.45, 559.47, 250/492.2, 201.3; 359/642, 351, 355, 365, 359/385
See application file for complete search history.

(56) References Cited

U.S. PATENT DOCUMENTS

| | | | | |
|---|---|---|---|---|
| 5,604,344 | A * | 2/1997 | Finarov | .................... 250/201.3 |
| 5,805,278 | A | 9/1998 | Danko | |
| 6,384,909 | B1 * | 5/2002 | Tomita et al. | ........... 356/237.1 |
| 6,407,373 | B1 * | 6/2002 | Dotan | ..................... 250/201.3 |
| 6,563,586 | B1 * | 5/2003 | Stanke et al. | ............... 356/445 |
| 6,621,570 | B1 | 9/2003 | Danko | |
| 6,661,580 | B1 * | 12/2003 | Solarz | ........................ 359/642 |
| 6,797,975 | B1 * | 9/2004 | Nishiyama et al. | .... 250/559.04 |

FOREIGN PATENT DOCUMENTS

JP            2003262782 A    *   9/2003

* cited by examiner

*Primary Examiner*—Gregory J. Toatley, Jr.
*Assistant Examiner*—Sang H. Nguyen
(74) *Attorney, Agent, or Firm*—Ann Marie Mewherter; Daffer McDaniel, LLP

(57) ABSTRACT

An apparatus for inspecting a semiconductor wafer includes a vertically movable chuck plate for holding said semiconductor wafer, a first light source for illuminating an area on the wafer, a main imaging camera for detecting light scattered from the surface of the wafer and a main imaging lens for imaging the illuminated area of the wafer onto the camera. The apparatus additionally includes an auto-focus system for maintaining the wafer within the depth of field of the lens focal point. The auto-focus system comprises a second light source with associated optics, a linear position sensor with associated optics for detecting light from the second light source that is reflected off the illuminated area of the wafer, circuitry for converting the light detected by the sensor into an output voltage which is proportional to the relative vertical position of the illuminated area of the wafer. In use, the output voltage can be used to compensate for vertical deviations in the topology of said patterned wafer by vertically moving the chuck plate in real-time so that the lens images the area on the wafer onto the camera in focus.

13 Claims, 2 Drawing Sheets

METHOD AND APPARATUS FOR INSPECTING A SEMICONDUCTOR WAFER

BACKGROUND OF THE INVENTION

The present invention relates generally to a novel method and apparatus for inspecting a semiconductor wafer for defects.

Integrated circuits (ICs) are commonly manufactured through a series of processing steps. Very often more than a hundred processing steps are performed to produce a properly functioning integrated circuit chip.

A semiconductor material, commonly in the shape of a wafer, serves as the substrate for integrated circuits. Semiconductor ICs are typically manufactured as an assembly of a hundred or more chips on a single semiconductor wafer which is then cut up to produce the individual IC chips. Typically, a wafer made of silicon is used as the integrated circuit substrate, the silicon wafer being approximately 150–300 mm in diameter and 0.6–1 mm thick. During the manufacturing process, the silicon wafer is first polished and cleaned to remove all contaminant particles situated thereon. The silicon wafer is then treated in preparation for a series of processing steps involving a plurality of photolithographic patterns (also commonly referred to as masks). In the production of integrated circuits, microelectronic circuits are formed onto the silicon wafer through a process of layering. In the layering process, conductive and insulated layers of thin films are deposited and patterned onto the silicon wafer. Each layer is patterned by a mask designed specifically for it, the mask defining the areas within the wafer that are to be treated such as by etching or implanting.

Semiconductor fabrication technology today deals with silicon wafers which are approximately 200 mm in diameter and which feature geometries with dimensions well below 0.5 µm (micrometer). Due to the high complexity and level of integration of integrated circuits, the absence of defects on every layer of the wafer is critical in order to realize acceptable levels of product yield. The most prevalent type of wafer pattern defect which occurs during the manufacturing of patterned semiconductor wafers is the improper deposition of conductive and/or insulated material onto the silicon wafer during the layering process. Additional types of wafer pattern defects include, inter alia, the presence of contaminant particles and/or scratches on the wafer during the manufacturing process.

As can be appreciated, the presence of a single defect larger than half the width of a conductive line on the silicon wafer can result in the complete failure of a semiconductor chip which is produced from the wafer. Such a chip has to be discarded which thereby decreases the percentage yield per wafer and increases the overall cost of the individual wafers. Therefore, a critical task facing semiconductor process engineers is to identify and, as soon as possible, to eliminate sources of defects on each layer of a semiconductor wafer.

Accordingly, wafer inspection systems are well known in the art and are commonly used to detect, identify and correct yield limiting defects which are introduced onto the surface of a semiconductor wafer during the fabrication process of integrated circuits. In fact, it is well known in the art for a plurality of wafer inspection systems to be used to inspect a semiconductor wafer at various points in time during the fabrication of said semiconductor wafer. As such, each wafer inspection system serves to inspect the semiconductor wafer after the treatment of a particular layer of the integrated circuit. By using multiple wafer inspection instruments to scan various layers of the semiconductor wafer for defects, the user is able to discern where, and more specifically on which layer, a defect first occurred during the manufacturing process. The ability to discern where a defect first occurred is extremely useful in removing the defect and in preventing future defects.

Wafer Inspection systems typically include at least one light source (e.g., a laser) which illuminates an area on the surface of the wafer. A main imaging camera is positioned directly above the surface of the wafer and detects light which is scattered from the area illuminated by the light source. A main imaging lens is disposed between the surface of the wafer and the main imaging camera and serves to image the illuminated area on the semiconductor wafer onto the main imaging camera. The main imaging camera is typically connected to an image processing computer which identifies and stores the location of each defect. A wafer defect map is then generated and displayed on a monitor or is used to track the defects through further processing layers. In this manner, a semiconductor process engineer is capable of locating the presence of defects on a semiconductor wafer by viewing the viewing screen of the monitor, which is highly desirable.

Wafer inspection systems of the type described above have been made commercially available by such companies as Inspex, Inc. of Billerica, Mass. The EAGLE™ wafer inspection system is one well known type of wafer inspection system which is manufactured and sold by Inspex, Inc. of Billerica, Mass. Examples of some well-known wafer inspection systems are shown in U.S. Pat. No. 6,621,570 and U.S. Pat. No. 5,805,278, which are both incorporated herein by reference.

Although well known and widely used in commerce to detect the presence of defects, conventional wafer inspection systems may suffer from a notable drawback. Specifically, the relatively high levels of magnification and optimization of the main imaging lens of a conventional wafer inspection system serves to significantly decrease the depth of field for the system (i.e., the allowable change in distance between the main imaging lens and the wafer surface while maintaining the wafer surface in focus). In fact, wafer inspection systems of the type described above have been found to have a depth of field in the order of approximately 2 microns.

However, it should be noted that wafer inspection systems commonly include a vacuum chuck for retaining the wafer to be inspected. In use, it has been found that a vacuum chuck can significantly deform an otherwise flat wafer mounted thereon. In fact, it has been found that vertical deviations in wafer topology can reach levels as high as 10 to 20 microns. Because vertical deviations in wafer topology are considerably greater than the depth of field of conventional wafer inspection systems, particular regions on a wafer scanned by a conventional wafer inspection system are often examined out of focus, which is highly undesirable.

Accordingly, it is the principal object of the present invention to provide a wafer inspection system with a dynamic, real-time auto-focusing system which can be used to vertically manipulate the wafer stage as deemed necessary to maintain each illuminated area on the wafer in focus regardless of whether the wafer is experiencing levels of considerable deformation.

SUMMARY OF THE INVENTION

It is an object of the present invention to provide a novel method and apparatus for inspecting a semiconductor wafer for defects.

It is another object of the present invention to provide a method and apparatus as described above which effectively illuminates an area of the semiconductor wafer for detection.

It is yet another object of the present invention to provide a method and apparatus as described above which includes a main imaging lens for imaging the illuminated area of the semiconductor wafer onto a main imaging camera.

It is yet another object of the present invention to provide a method and apparatus as described above which includes a dynamic, real-time auto-focusing system for ensuring that the main imaging lens images the illuminated area of the semiconductor wafer onto the main imaging camera in focus.

It is still another object of the present invention to provide a method and apparatus as described above which has a limited number of parts and which is easy to use.

Accordingly, there is provided an apparatus for inspecting a semiconductor wafer, said apparatus comprising a first light source for producing a first beam of light, said first beam of light illuminating an area on the semiconductor wafer, a main imaging camera disposed above the wafer for detecting light scattered from the area illuminated by the first beam of light, and a main imaging lens for imaging the area on the semiconductor wafer illuminated by the first beam of light onto said main imaging camera, and an auto-focus system to compensate for vertical deviations in the topology of said semiconductor wafer, said auto-focus system ensuring that said main imaging lens images the area on said semiconductor wafer onto said main imaging lens in focus, said auto-focus system comprising a second light source for producing a second beam of light, said second beam of light reflecting off the area on the semiconductor wafer, and a sensor for detecting light reflected from the semiconductor wafer by the second beam of light.

Various other features and advantages will appear from the description to follow. In the description, reference is made to the accompanying drawings which form a part thereof, and in which is shown by way of illustration, a specific embodiment for practicing the invention. The embodiment will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF THE PREFERRED EMBODIMENT

Figure 1:
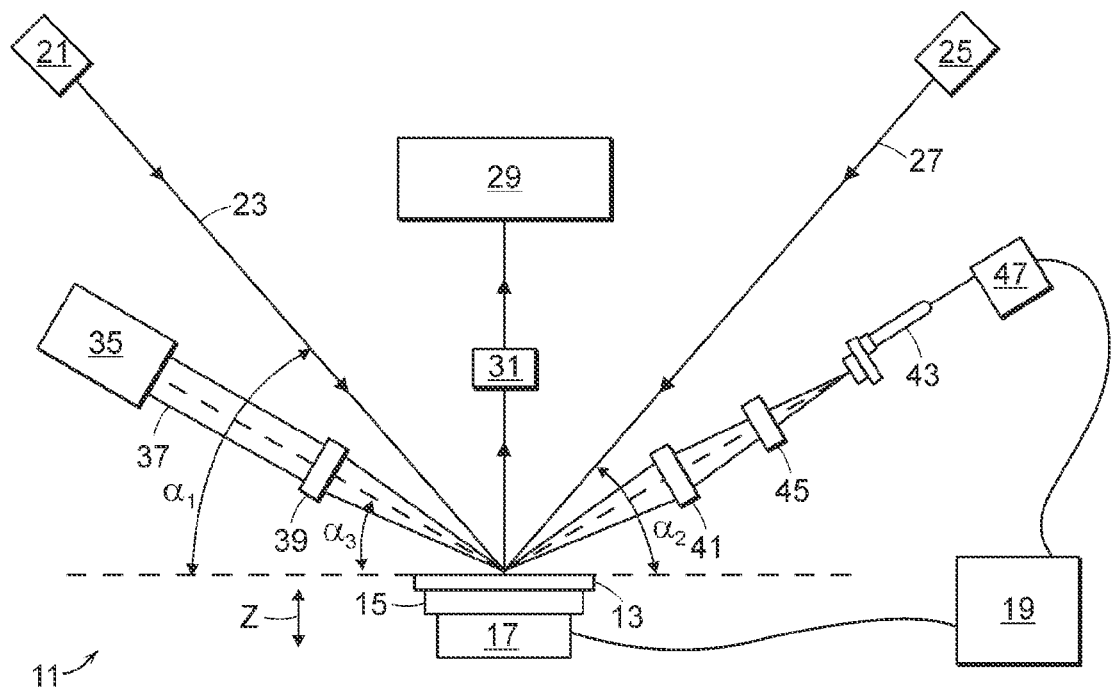
FIG. 1 is a schematic side view representation of an apparatus for inspecting a semiconductor wafer for defects, said apparatus being constructed according to the teachings of the present invention.

Referring now to FIG. 1, there is shown a schematic side view representation of an apparatus for inspecting a semiconductor wafer for defects. The apparatus is constructed according to the teachings of the present invention and is identified generally by reference numeral 11.

Apparatus 11 is shown inspecting a semiconductor wafer 13. Wafer 13 represents any well-known type of semiconductor wafer, such as a patterned semiconductor wafer.

Semiconductor wafer 13 is retained on a chuck plate 15. Chuck plate 15 is preferably a vacuum chuck plate which is capable of providing a vacuum force for retaining semiconductor wafer 13 securely thereon. Chuck plate 15 is mounted on a stage 17 which is capable of displacing chuck plate 15 in three dimensions (i.e., stage 17 is an X-Y-Z stage), stage 17 being electrically connected to a computer 19. Preferably, stage 17 is a linear motor air-bearing X-Y motion platform which utilizes piezoelectric elements to move chuck plate 15 in the Z dimension. However, it is to be understood that stage 17 could use alternative means for displacing plate 15 in the Z dimension (e.g., magnetic and/or voice coil means) without departing from the spirit of the present invention.

As will be described further in detail below, the ability of stage 17 to move chuck plate 15 in the vertical dimension (i.e., in the Z dimension as represented by arrow Z in FIG. 1) enables patterned semiconductor wafer 13 to be adjusted, as deemed necessary, into alignment with the focal point of a main imaging lens.

Apparatus 11 includes a first light source 21 which is preferably in the form of a laser. Light source 21 produces a first beam of light 23 which illuminates an area, or region, of semiconductor wafer 13. Light source 21 is preferably mounted such that first beam of light 23 illuminates an area of wafer 13 at a grazing angle $\alpha_1$ which can be adjusted between approximately 0–45 degrees.

Apparatus 11 may optionally include a second light source 25 which is preferably in the form of a laser. Light source 25 produces a second beam of light 27 which illuminates the same area of semiconductor wafer 13 that is illuminated by first beam of light 23. Light source 25 is preferably mounted such that second beam of light 27 illuminates the target area of wafer 13 at a grazing angle $\alpha_2$ which can be adjusted between approximately 0–45 degrees.

Together, first and second beams of light 23 and 27 illuminate an area on semiconductor wafer 13. Based on well-known principles of scattered light, defects present on the surface of the area on semiconductor wafer 13 will refract the light from first and second beams of light 23 and 27.

A main imaging camera 29, such as a high sensitivity video camera, is positioned directly above the surface of semiconductor wafer 13. As can be appreciated, main imaging camera 29 is designed to detect light which is scattered from the area of wafer 13 that is illuminated by light sources 21 and 25. Preferably, main imaging camera 29 is electrically connected to an image processor and monitor (not shown) which, in turn, displays an image based on the number of photons which disperse from the area on the surface of the wafer. In this capacity, patterns and defects present on the surface of wafer scatter light provided by light sources 21 and 25 onto main imaging camera 29 which, in turn, presents the defect location as an image on the monitor, which is highly desirable.

A main imaging lens 31 is disposed between the surface of semiconductor wafer 13 and main imaging camera 29.

Main imaging lens 31 is preferably a high magnification lens which serves to image the illuminated area on semiconductor wafer 13 onto main imaging camera 29. As can be appreciated, the surface of the illuminated area on semiconductor wafer 13 is preferably located at the focal point for main imaging lens 31, thereby ensuring that the illuminated area on wafer 13 is imaged onto main imaging camera 29 in focus.

Due to its relatively high level of magnification and optimization, main imaging lens 31 is provided with a relatively limited depth of field of approximately 2 microns. Stated another way, the surface of the illuminated area on patterned semiconductor wafer 13 can not deviate from the focal point of main imaging lens 31 a distance which is greater than the depth of field (approximately 2 microns) without compromising the ability of main imaging lens 31 to image the illuminated area on wafer 13 onto main imaging camera 29 in focus.

However, it should be noted that the surface of wafer 13, when mounted on chuck plate 15, is not perfectly flat. Rather, it has been found that the surface of wafer 13 can become considerably deformed when mounted on vacuum chuck plate 15. In fact, it has been found that vertical deviations in the topology of a semiconductor wafer 13 mounted on a vacuum chuck plate can approach levels as high as approximately 10–20 microns. Because vertical deviations in the topology of a wafer 13 mounted on chuck plate 15 are considerably greater than the depth of field of main imaging lens 31, in the absence of an auto-focusing system, particular regions on wafer 13 would be imaged by main imaging lens 31 onto main imaging camera 29 out of focus, which is highly undesirable.

Accordingly, apparatus 11 is provided with an auto-focus system 33 for vertically displacing wafer chuck plate 15 in real time (in the Z-dimension as represented by arrow Z in FIG. 1) when necessary to maintain each illuminated area on semiconductor wafer 13 which is imaged onto main imaging camera 29 in focus. In particular, auto-focus system 33 maintains each illuminated area on wafer 13 which is imaged onto camera 29 in focus by vertically displacing chuck plate 15 either towards or away from lens 31 until said area is located at the focal point for lens 31, as will be described further below.

Figure 2:
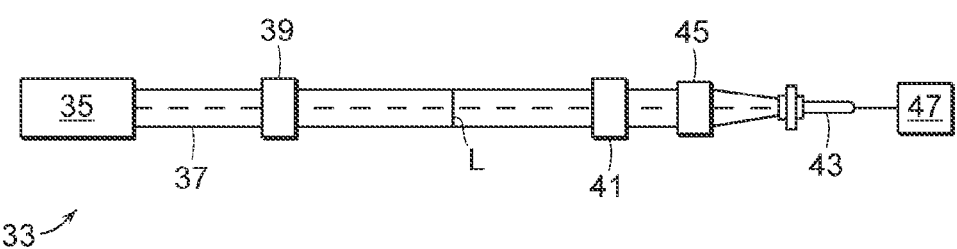
FIG. 2 is a schematic top view representation of the auto-focus system shown in FIG. 1.

Referring now to FIGS. 1 and 2, auto-focus system 33 comprises a third light source 35 which is preferably in the form of a laser. Light source 35 produces a collimated beam of light 37 which has fixed horizontal and vertical beam widths. Light source 35 is preferably mounted such that beam of light 37 reflects off the illuminated area of semiconductor wafer 13 at a grazing angle $\alpha_3$ which is low enough to avoid interference with the lowest possible position of main imaging lens 31. As can be appreciated, since the reflection of beam of light 37 will be influenced by both the relative vertical position and the angle of the illuminated area of wafer 13, optics are required to isolate the vertical position information relating to the illuminated area of wafer 13 without being corrupted by the angle of the illuminated area of wafer 13.

Accordingly, a lens 39 is provided between light source 35 and semiconductor wafer 13. Lens 39 is preferably a cylindrical lens which affects beam of light 37 only along its vertical axis. Specifically, lens 39 serves to focus beam of light 37 to a point along its vertical axis at the illuminated area of semiconductor wafer 13, as seen most clearly in FIG. 1. As a result, beam of light 37 reflects off of the illuminated area of wafer 13 as a line L, as seen most clearly in FIG. 2. It should be noted that system 33 focuses collimated beam of light 37 to a line on the surface of wafer 13 by locating lens 39 a distance away from the point of beam contact with the surface of wafer 13 which is equal to the focal length of lens 39.

After beam of light 37 reflects off semiconductor wafer 13, beam of light 37 diverges along its vertical axis, as seen most clearly in FIG. 1. A lens 41 is provided to image the point source of the reflected beam of light 37 onto the surface of a single-axis linear position sensor 43. As can be appreciated, the position of the point source of the reflected beam of light 37 onto the surface of sensor 43 is dictated only by the relative vertical position of the illuminated area of semiconductor wafer 13, which is highly desirable.

Specifically, any angular variation in the illuminated surface of wafer 13 will result in beam of light 37 reflecting off wafer 13 at a different angle. However, even though light 37 reflects off wafer 13 at a different angle, lens 41 still properly images the reflected beam of light 37 onto linear position sensor 43, thereby enabling the vertical position of the illuminated area of wafer 13 to be identified, which is highly desirable. It should be noted that the maximum allowable angular deviation in the surface of wafer 13 that can still be properly imaged onto linear position sensor 43 is limited by the divergence angle of the reflected beam of light and the light collecting capacity of lens 41 (i.e., the diameter and spherical aberrations of lens 41).

A lens 45 is positioned between lens 41 and linear position sensor 43. Lens 45 is preferably a cylindrical lens which affects beam of light 37 only along its horizontal axis. Specifically, as seen most clearly in FIG. 2, beam of light 37 is a collimated light beam with a fixed horizontal beam width. Because lens 39 has no affect on light beam 37 in the horizontal axis, light beam 37 reflects off wafer 13 to form an illumination line. Light beam 37 remains collimated with a fixed horizontal beam width until light beam 37 reaches lens 45. Lens 45, in turn, focuses light beam 37 onto linear position sensor 43.

It should be noted that lens 45 does not focus light beam 37 to a point on sensor 43. Rather, lens 45 focuses light beam 37 to a narrow horizontal line on sensor 43, the horizontal line having a width which is approximately the same as the width of the active sensing area of sensor 43 to prevent the energy density of light beam 37 from exceeding the damage threshold of linear position sensor 43. This allows sensor 43 to track the weighted average of the illuminated line on semiconductor wafer 13. As a result, since the features of the illuminated surface of semiconductor wafer 13 are small in area and may include different heights, tracking the weighted average enables system 33 to maintain the majority of the illuminated surface of wafer 13 within the acceptable range of the focal plane of imaging lens 31, which is highly desirable.

Circuitry 47 is electrically connected to linear position sensor 43 and serves to convert the relative position of beam of light 37 on sensor 43 to a corresponding voltage. In other words, circuitry 47 serves to produce an output voltage which is directly proportional to the relative vertical position of beam of light 37 on sensor 43.

Figure 3:
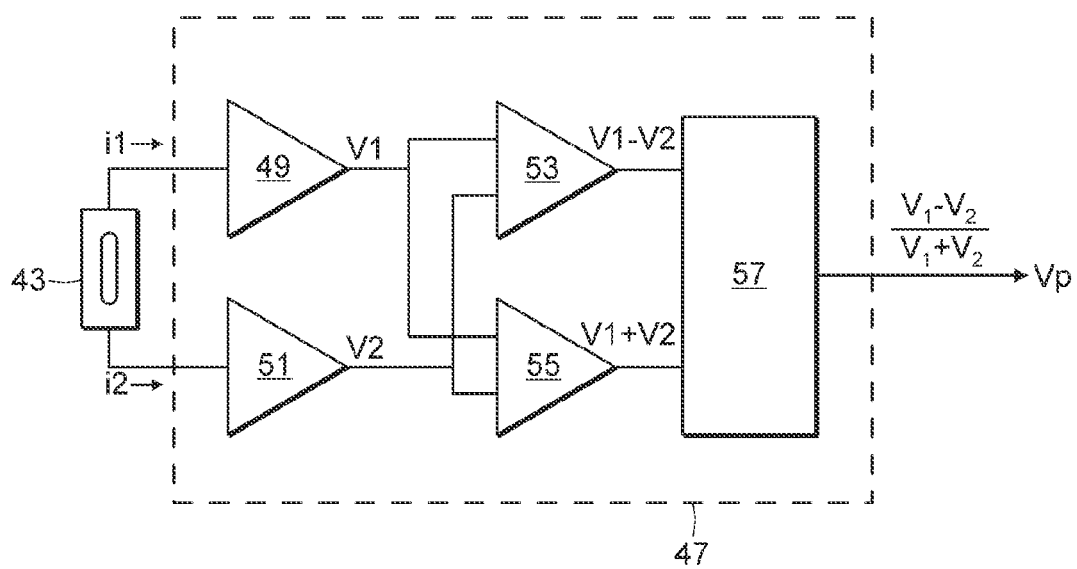
FIG. 3 is a detailed functional representation of the linear position sensor and circuitry shown in FIG. 1.

Referring now to FIG. 3, there is shown a detailed functional representation of circuitry 47 and sensor 43. As can be appreciated, sensor 43 is reverse-biased so that it behaves in a photoconductive mode. In this mode, sensor 43 produces first and second currents $i1$ and $i2$. Each of currents $i1$ and $i2$ has an amplitude that is proportional to the position of the weighted average of the light spot on sensor 43 in the vertical dimension. The sum of currents $i1$ and $i2$ is proportional to the intensity of the light spot on sensor 43.

First and second trans-impedance amplifiers 49 and 51 are connected to the terminals of linear position sensor 43. First trans-impedance amplifier 49 serves to convert current i1 to a proportional voltage V1. Similarly, second trans-impedance amplifier 51 serves to convert current i2 to a proportional voltage V2.

A differential amplifier 53 is connected to first and second trans-impedance amplifiers 49 and 51. In operation, differential amplifier 53 generates an output signal which is equal to the difference of V1 and V2 (i.e., V1−V2). Similarly, a summing amplifier 55 is connected to first and second trans-impedance amplifiers 49 and 51. In operation, summing amplifier 55 generates an output signal which is equal to the sum of V1 and V2 (i.e., V1+V2).

An analog divider 57 is connected to the output nodes of differential and summing amplifiers 53 and 55. In operation, analog divider 57 generates an output, or divider, voltage Vp which is the real-time quotient of the output signals of differential and summing amplifiers 53 and 55 (i.e., (V1−V2)/(V1+V2)).

As can be appreciated, output voltage Vp is directly proportional to the position of the weighted average of the light spot on linear position sensor 43 independent of the light intensity which, in turn, is directly related to the vertical position of the illuminated area of wafer 13. As a result, the sensing method is not affected by variations in the intensity of the reflected light due to variations in reflectivity of the surface of wafer 13.

It should be noted that the use of linear position sensor 43 allows for auto-focus system 33 to dynamically retain semiconductor wafer 13 in focus on main imaging camera 29 in real-time using either of the following modes of auto-focus operation.

In the first mode of operation, light source 35 provides a light beam 37 which reflects off of the illuminated area of wafer 13 and onto linear position sensor 43 in the manner described in detail above. In turn, the circuitry 47 converts the point of light on sensor 43 into a voltage Vp which is directly proportional to the vertical position, or height, of the illuminated area on wafer 13. Computer 19 then analyzes the real-time value of voltage Vp and, in response thereto, regulates the operation of piezo stage 17. Specifically, piezo stage 17 vertically displaces chuck plate 15 (and wafer 13) until the output voltage Vp reaches a pre-determined constant value (e.g., zero). As a result, the height of the illuminated area of wafer 13 is corrected, as deemed necessary, to maintain the imaging of the illuminated area of wafer 13 onto camera 29 by lens 31 in focus, which is the primary objective of the present invention.

It should be noted that the first mode described above is the preferred means for auto-focus operation. However, it has been found that the first mode does not function properly on a semiconductor wafer 13 which is coated so as not to reflect light. As a result, beam of light 37 produced by light source 35 will not reflect onto sensor 43, thereby precluding auto-focus system 33 from properly operating.

Accordingly, in the second mode of operation (i.e., for the auto-focusing of a non-reflective wafer), a bare wafer is mounted onto chuck plate 15. The Z axis of stage 17 is held stationary. The wafer is scanned in the X-Y dimensions while the sensor output voltage (Vp) is sampled by computer 19. The results of said operation serve to create a three dimensional surface contour map for the bare wafer, the three-dimensional surface contour map of the bare wafer being stored in a look-up table in computer 19. Because the deformation of wafer 13 on chuck plate 15 is due primarily to imperfections in the construction and operation of chuck plate 15, a non-reflective wafer would have substantially the same surface contour as a bare wafer. Consequently, when a non-reflective wafer is mounted on chuck plate 15, the three-dimensional surface contour map of a bare wafer (which can be readily retrieved from the look-up table in computer 19) can be used to maintain the vertical position of selected regions on the non-reflective wafer in focus, which is highly desirable.

It should be noted that linear position sensor 43 enables auto-focus system 33 to perform both modes of auto-focusing operation described above. However, it is to be understood that linear position sensor 43 could be replaced with alternative types of sensors without departing from the spirit of the present invention.

For example, linear position sensor 43 could be replaced with a bi-cell (or split-cell) sensor without departing from the spirit of the present invention. A bi-cell sensor would comprise two independent sensing areas which are separated by a small non-sensing area. As can be appreciated, a bi-cell sensor will not give a linear output signal relative to the position of the weighted average (or the wafer surface height) but will depend on the beam intensity distribution relative to the dimensions of the bi-cell sensing areas. As a result, a bi-cell sensor can be used in the first auto-focusing mode of operation (i.e., for a reflective wafer), where the vertical position of the illuminated area of wafer 13 is to be adjusted vertically by piezo stage 17 to maintain the output signal Vp at a constant value. However, the bi-cell sensor can not be used in the second auto-focusing mode of operation (i.e., for a non-reflective wafer) by generating a three-dimensional contour map of a bare wafer because the output signal Vp would not be linear with respect to the height of the illuminated area of the surface of wafer 13.

It should also be noted that auto-focus system 33 is not limited for use in conjunction with the inspection of a semiconductor wafer for defects. Rather, it is to be understood that auto-focus system 33 could be implemented in any system which requires the real-time, dynamic, focusing of an object without departing from the spirit of the present invention.

The embodiment shown of the present invention is intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. An apparatus for inspecting a semiconductor wafer, said apparatus comprising:
   (a) a first light source for producing a first beam of light, said first beam of light illuminating an area on the semiconductor wafer,
   (b) a main imaging camera disposed above the semiconductor wafer for detecting light scattered from the area illuminated by the first beam of light, and
   (c) a main imaging lens for imaging the area on the semiconductor wafer illuminated by the first beam of light onto said main imaging camera, and
   (d) an auto-focus system to compensate for vertical deviations in the topology of said semiconductor wafer, said auto-focus system ensuring that said main imaging lens images the area on said semiconductor wafer onto said main imaging camera in focus, said auto-focus system comprising, (i) a second light source with associated optics for producing a second beam of light, said second beam of light reflecting off the area on the semiconductor wafer, (ii) a sensor with associated optics for detecting light reflected from the semiconductor wafer by the second beam of light, wherein said sensor is a linear position sensor; and (iii) circuitry for converting the light detected by said linear position sensor into a voltage which is proportional to the relative vertical position of the area of the semiconductor wafer.

2. The apparatus as claimed in claim 1 further comprising a chuck plate which is adapted to retain the semiconductor wafer.

3. The apparatus as claimed in claim 2 further comprising a stage for displacing said chuck plate.

4. The apparatus as claimed in claim 3 wherein said stage is adapted to displace said chuck plate towards and away from said main imaging lens.

5. The apparatus as claimed in claim 4 wherein said stage is adapted to displace said chuck plate in three dimensions.

6. The apparatus as claimed in claim 4 wherein said second beam of light is collimated with fixed horizontal and vertical beam widths.

7. The apparatus as claimed in claim 6 wherein said auto-focus system additionally comprises:

(a) a first lens positioned between said second light source and the semiconductor wafer, said first lens focusing the second beam of light along its vertical axis, (b) a second lens positioned between the semiconductor wafer and said sensor, said second lens focusing the second beam of light along its vertical axis, and (c) a third lens positioned between the semiconductor wafer and said sensor, said third lens focusing the second beam of light along its horizontal axis.

8. The apparatus as claimed in claim 1, wherein said sensor is reversed-biased to produce first and second currents in response to detecting light reflected from the semiconductor wafer by the second beam of light.

9. The apparatus as claimed in claim 8 wherein said circuitry comprises:

(a) a first trans-impedance amplifier for converting the first current into a proportional first voltage, (b) a second trans-impedance amplifier for converting the second current into a proportional second voltage, (c) a differential amplifier connected to said first and second trans-impedance amplifiers, said differential amplifier producing a differential voltage equal to the difference between the first voltage and the second voltage, (d) a summing amplifier connected to said first and second trans-impedance amplifiers, said summing amplifier producing a summing voltage equal to the sum of the first voltage and the second voltage, and (e) an analog divider connected to said differential and summing amplifiers, said analog divider generating a divider voltage which is proportional to the quotient of the differential voltage and the summing voltage.

10. The apparatus as claimed in claim 9 wherein the divider voltage is directly proportional to the vertical position of the illuminated area of said semiconductor wafer.

11. The apparatus as claimed in claim 10 further comprising a computer connected to said circuitry, said computer being adapted to regulate the relative position of said semiconductor wafer based on the value of the divider voltage.

12. A method for inspecting an area of a semiconductor wafer using a wafer inspection apparatus, said wafer inspection apparatus comprising a first light source for producing a first beam of light, said first beam of light illuminating an area on the semiconductor wafer, a main imaging camera disposed above the semiconductor wafer for detecting light scattered from the area illuminated by the first beam of light, and a main imaging lens for imaging the area on the semiconductor wafer illuminated by the first beam of light onto said main imaging camera, and an auto-focus system comprising a second light source for producing a second beam of light, said second beam of light reflecting off the area on the semiconductor wafer, and a sensor for detecting light reflected from the semiconductor wafer by the second beam of light, said method comprising the steps of:

(a) examining the vertical position of the illuminated area of said semiconductor wafer using said auto-focus system, said auto-focus system yielding an output voltage in response thereto, and (b) displacing the relative vertical position of the illuminated area of said semiconductor wafer using said output voltage.

13. A method for inspecting an area of a first semiconductor wafer using a wafer inspection apparatus, said wafer inspection apparatus comprising a first light source for producing a first beam of light, said first beam of light illuminating an area on the first semiconductor wafer, a main imaging camera disposed above the first semiconductor wafer for detecting light scattered from the area illuminated by the first beam of light, and a main imaging lens for imaging the area on the first semiconductor wafer illuminated by the first beam of light onto said main imaging camera, and an auto-focus system comprising a second light source for producing a second beam of light, said second beam of light reflecting off the area on the first semiconductor wafer, and a sensor for detecting light reflected from the first semiconductor wafer by the second beam of light, said method comprising the steps of:

(a) providing a second semiconductor wafer, (b) examining the second wafer using said auto-focus system so as to yield a surface contour map for said second wafer, and (c) examining the first semiconductor wafer using said wafer inspection apparatus, wherein the position of the first patterned semiconductor wafer is displaced relative to said imaging lens based upon the surface contour map for said second wafer.

* * * * *